United States Patent [19]

Burns

[11] Patent Number: 4,529,614

[45] Date of Patent: Jul. 16, 1985

[54] ONE STEP ANTICOAGULANT COATING

[75] Inventor: James A. Burns, Elizabeth, N.J.

[73] Assignee: Becton, Dickinson and Company, Paramus, N.J.

[21] Appl. No.: 326,712

[22] Filed: Dec. 2, 1981

[51] Int. Cl.³ ............................................. A01N 43/16
[52] U.S. Cl. .................................. 427/2; 215/DIG. 3; 424/78; 514/63
[58] Field of Search ................. 424/78, 184, 101, 186; 215/DIG. 3; 422/102; 427/2

[56] References Cited

PUBLICATIONS

Science, vol. 152, pp. 1625–1626, Jun. 17, 1966.

Primary Examiner—Sam Silverberg
Attorney, Agent, or Firm—Robert P. Grindle

[57] ABSTRACT

This invention relates to single-step coating methods for coating substrates such as plastics or glass to impart properties to the substrate which are anticoagulant and hydrophobic, and to substrates so coated. The method is particularly useful in coating the internal surfaces of blood test vessels, such as microcontainers or VACUTAINERS® for receiving blood samples for subsequent testing. The method herein imparts the desired properties to the vessel in a single step by combining silicone containing material in a water vehicle to which has been added a quantity of an anticoagulant, such as heparin or ethylene diamine tetraacetic acid (EDTA), followed by air drying.

9 Claims, No Drawings

ONE STEP ANTICOAGULANT COATING

BACKGROUND AND DESCRIPTION OF THE INVENTION

Generally speaking, this invention relates to a method for imparting an anticoagulant coating to a substrate. More particularly, this invention relates to a one coating step method for imparting a coating to a substrate surface which coating is water soluble but which, nevertheless, has combined hydrophobic/anticoagulant properties. The surface is particularly useful in a blood test container for receiving blood samples for subsequent testing.

As will be appreciated, with the ever increasing use of chemistry for testing human blood, larger quantities of vessels for receiving the blood for the many tests being carried out must be produced. It is economical, under these circumstances, to produce, on a production line basis, many thousands of such vessels for receiving the various test samples. As will be appreciated, once the vessels are used a single time, they are discarded so as to avoid contamination. It is important, in the production of such vessels to impart the desired properties to the surfaces thereof in as few steps as possible in order to produce the vessels in an acceptable economic fashion. As will be appreciated further, the fewer steps, the cheaper the production line operation for producing the resulting objects.

In the past, in order to impart surfaces with combined properties to the internal surfaces of blood test vessels, such as a microcontainer or a VACUTAINER®, it was necessary to impart first the hydrophobic property to the internal surface of the vessel, with a subsequent activation or heating step, followed by a separate coating step for imparting the second property to the internal surface. From the above discussion, it will be appreciated that the separate steps involved increase the cost of production of each item being produced.

With this invention, by contrast, it has now been found that a combined coating can be imparted to a substrate, which resulting coating will provide the desired anticoagulant and hydrophobic properties to the substrate being coated. Quite unexpectedly, it has been found that a heparin compound or ethylene diamine tetraacetic acid may be combined with a silicone containing material in a water vehicle, such as deionized water, and the resulting solution applied to the internal surface of the vessles under consideration. A subsequent drying step which may be a simple air drying or an air jet at low velocity and temperature for a short duration achieves the resulting dried coating having simultaneously the desired properties. In this connection, while the properties of the resulting coating are not completely understood, it is believed that a combined anticoagulant/organopolysiloxane prepolymer matrix is mechanically fixed to the substrate of interest. Thus, with the addition of blood, the mechanical coating dissolves in the blood to the extent necessary to impart anticoagulant properties to the sample. Nevertheless, the organopolysiloxane provides sufficient flow for the blood to impart hydrophobicity to the surface of the substrate of interest, with the result being that the blood will flow freely into and out of a microcontainer, for example.

Accordingly, it is one object of this invention to provide a method for coating the internal surfaces of blood test vessels such as microcontainers in order to impart to the internal surfaces thereof an anticoagulant property and a hydrophobic property. A further object of the invention is to provide the coatings in a one-step process wherein the properties are imparted to the substrate simultaneously. A further object of the invention is to provide such coated substrates at reduced costs because of the reduction in the number of steps involved in imparting the desired resulting surface.

With the foregoing and additional objects in view, this invention will now be described in more detail, and other objects and advantages will be apparent from the following description, and the appended claims.

Before describing this invention in more detail, it may be well to note that this invention has been found applicable to a wide variety of substrates including, for example, glass, resin materials such as polyethylene, acrylonitrile-butadiene-styrene terpolymer, polystyrene, nylon and acetal as well as other substrate materials wherein it is desirable to impart to the surface thereof a coating with combined anticoagulant-hydrophobic properties in the manner as discussed above.

In considering generally the conditions for achieving the most enhanced results in connection herewith, which conditions are more specifically set forth below, one may note that satisfactory coated surfaces are achieved in accordance herewith with a 1% solution of a silicone containing material such as an organopolysiloxane in deionized water to which has been added a 0.2% solution of ammonium heparin or ethyelene diamine tetraacetic acid. Each of the containers to be coated is exposed internally to the coating solution followed by the application of a low velocity air jet at 200° F.

A preferred cycle of operation, in accordance herewith, for formulating the desired combined coating on the internal surfaces of microcontainers, for example, includes utilizing an automatic production line and imparting the coating as described above to the internal surfaces of each of the microcontainers passing along the production line with the coating solution being formulated in parts by weight from within the range of between about 0.2 parts ammonium heparin to 0.8 parts ammonium heparin, and within the range of between about 0.9920 parts organopolysiloxane to 0.9980 parts, and within the range of between about 98.208-98.802 parts deionized water. In this connection, the organopolysiloxane may be "L520" silicone supplied by Union Carbide or "DC193", a product of Dow Corning. Most preferably, the coating solution will contain within the range of between about 0.5-0.55 parts ammonium heparin, 0.9945-0.9950 parts an organopolysiloxane and 98.455 parts-98.505 parts deionized water. The results of such a coating operating are individual microcontainer tubes having imparted to the internal surface thereof an organopolysiloxane coating with within the range of between about 8.5-9.35 units of heparin.

Alternatively, if a combined EDTA and silicone coating is desired, preferably the coating solution will include in parts by weight within the range of between about 1.4 parts-5 parts EDTA, and most preferably 3.1 parts-5 parts, within the range of between about 0.950 parts organopolysiloxane-0.986 parts, and most preferably 0.950-0.969, and within the range of between about 94.050 parts and 97.614 parts deionized water, and most preferably 94.05-95.931 parts deionized water.

The many tests achievable with microcontainers and coated in accordance herewith include, for example, in heparinized coatings according to this invention, tests for sodium content in the blood, potassium, bilirubin, glucose, BUN, creatinine, chloride and $CO_2$. The tests for the EDTA coated tubes include, for example, WBC, RBC, Hgb, Hct, MCV, MCH and MCHC.

It is to be understood that while the method of the invention herein was specifically developed to coat microcontainers for subsequent use in a series of different blood tests, this invention is not directed only to such microcontainers but may be applied to any vessel wherein it is desired to have on the internal surface thereof, a coating with the combined anticoagulant/hydrophobic properties discussed above which coating will readily dissolve in added blood and which will cause blood to flow readily over the coated surface. Moreover, it will be appreciated that other vessels and/or containers such as tubing may have imparted to the internal surfaces thereof a coating, in accordance herewith, for imparting the desired properties, as discussed herein.

As purely illustrative of the enhanced results achieved, in accordance herewith, one may note the following examples in which a plurality of microcontainer tubes were coated with various portions of the materials, as noted. In each case, the tube being coated is a polypropylene tube and the coating is applied to the walls. The coating was prepared by dissolving a salt of ethylene diamine tetraacetic acid or heparin in an aqueous solution containing 1% organopolysiloxane, rinsing the tube walls with the mixture and drying for a period of time within the range of between about 5 and 20 seconds, and preferably 12 seconds with a low velocity air jet at an elevated temperature within the range of between about 175° F.–225° F., and preferably about 200° F. Alternatively, the coating may be air dried at ambient if time is not a factor.

With respect to the first eight examples noted below, the tubes were coated with the anticoagulant heparin in the form of ammonium heparin at a potency of 68 units per milligram dissolved in an aqueous solution containing 1% L520 silicone. With respect to examples 9–14, the tubes were similarly coated with ammonium heparin at a potency of 75.8 units per milligram in the proportions noted. With respect to examples 15–19, the tubes were coated with sodium ethylene diamine tetraacetic acid dissolved in an aqueous solution containing 1% of L520 silicone in the proportions noted.

EXAMPLE 1

0.20 parts heparin, 0.998 parts silicone; and 98.802 parts water. Resulting heparin in coating: 3.4 units.

EXAMPLE 2

0.25 parts heparin, 0.9975 parts silicone, and 98.7525 parts water. Resulting heparin coating: 4.25 units.

EXAMPLE 3

0.3 parts heparin, 0.997 parts silicone, and 98.703 parts water. Resulting heparin coating: 5.1 units.

EXAMPLE 4

0.35 parts heparin, 0.9965 parts silicone and 98.6535 parts water. Resulting heparin coating: 5.95 units.

EXAMPLE 5

0.4 parts heparin, 0.996 parts silicone and 98.604 parts water. Resulting heparin in coating: 6.8 units.

EXAMPLE 6

0.45 parts heparin, 0.9955 parts silicone and 98.5545 parts water. Resulting heparin in coating: 7.65 units.

EXAMPLE 7

0.5 parts heparin, 0.995 parts silicone and 98.505 parts water. Resulting heparin in coating: 8.5 units.

EXAMPLE 8

0.55 parts heparin, 0.9945 parts silicone and 98.4555 parts water. Resulting heparin in coating: 9.35 units. Tubes were similarly coated with ammonium heparin at a potency of 75.8 units per mg. in the following proportions:

EXAMPLE 9

0.55 parts heparin, 0.9945 parts silicone and 98.4555 parts water. Resulting heparin in coating: 10.4 units.

EXAMPLE 10

0.6 parts heparin, 0.994 parts silicone and 98.406 parts water. Resulting heparin in coating: 11.4 units.

EXAMPLE 11

0.65 parts heparin, 0.9935 parts silicone and 98.3565 parts water. Resulting heparin in coating: 12.3 units.

EXAMPLE 12

0.7 parts heparin, 0.993 parts silicone and 98.307 parts water. Resulting heparin in coating: 13.3 units.

EXAMPLE 13

0.75 parts heparin, 0.9925 parts silicone and 98.2575 parts water. Resulting heparin in coating: 14.2 units.

EXAMPLE 14

0.8 parts heparin, 0.992 parts silicone, and 98.208 parts water. Resulting heparin in coating 15.2 units. Tubes were similarly coated with EDTA, with sodium ethylene diamine tetraacetic acid in an aqueous solution containing 1% of L520 silicone.

EXAMPLE 15

1.4 parts EDTA, 0.986 parts silicone and 97.614 parts water. Resulting EDTA content: 0.35 mg.

EXAMPLE 16

2.1 parts EDTA, 0.979 parts silicone and 96.921 parts water. Resulting EDTA content: 0.525 mg.

EXAMPLE 17

3.1 parts EDTA, 0.969 parts silicone and 95.931 parts water. Resulting EDTA content: 0.775 mg.

EXAMPLE 18

4.1 parts EDTA, 0.959 parts silicone and 94.941 parts water. Resulting EDTA content: 1.025 mg.

EXAMPLE 19

5 parts EDTA, 0.950 parts silicone and 94.05 parts water. Resulting EDTA content: 1.25 mg.

While all of the coatings produced in the first fourteen examples resulted in coatings with the desired combined properties, Examples 7 and 8, which are representative of the preferred range of heparin content in the coatings, in accordance herewith, provided the most satisfactory results for chemistry determinations using capillary blood for the sodium, potassium, chloride, $CO_2$, bilirubin, BUN, glucose, and creatinine tests noted above. Moreover, while all of the EDTA containing coatings also provided the desired combined anticoagulant/hydrophobic properties, Examples 17-19, containing the preferred quantities of EDTA, produced the most satisfactory results for hemotology determinations using capillary blood for the tests of WBC, RBC, Hgb, Hct, MCV, MCH and MCHC.

Accordingly, and as will be apparent from the foregoing, there are provided, in accordance herewith, methods and compositions for imparting to a variety of substrates, combined properties noted above which coatings are particularly useful for blood test containers, and more importantly, microcontainers for a variety of different blood tests which microcontainers can be subsequently disposed of. Further, because of the relative ease of operation in accordance herewith, in imparting simultaneously the desired dual properties to the surfaces involved, the method, in accordance herewith, is highly advantageous commercially, particularly for mass production techniques.

While the methods and compositions herein disclosed form preferred embodiments of this invention, this invention is not limited to those specific methods and compositions, and changes can be made therein without departing from the scope of the invention which is defined in the appended claims.

What is claimed is:

1. A method for coating substrates which coating readily dissolves in blood to provide simultaneously an anticoagulant property and a hydrophobic property, characterized by the steps of
   (a) preparing a coating solution comprising admixing
      (1) a liquid vehicle for said solution;
      (2) a member selected from the group consisting of a heparin compound and ethylene diamine tetraacetic acid; and
      (3) a silicone containing material;
   (b) selecting a substrate to be coated;
   (c) applying said coating solution from said preparing step to said substrate from said selecting step; and
   (d) drying said applied coating by applying an air jet to the coated substrate at an elevated temperature for a period of time within the range of between about 5 and 20 seconds.

2. The method of claim 1, further characterized by
   (a) said liquid vehicle in said preparing step is deionized water, and
   (b) said silicone containing material is an organopolysiloxane.

3. The method of claim 1, further characterized by
   (a) said substrate is a member selected from the group consisting of glass, polyethylene, polypropylene, polystyrene, acrylonitrile-butadiene-styrene terpolymer, an acetal, and nylon.

4. The method of claim 1, further characterized by
   (a) said drying step being carried out at a temperature within the range of between about 175° F. and 225° F.

5. The method of claim 4, further characterized by
   (a) said temperature is about 200° F., and said time is 12 seconds.

6. The method of claim 1, further characterized by
   (a) said preparing step is carried out by admixing by weight
      (1) within the range of between about 98.208 parts and 98.802 parts deionized water;
      (2) within the range of between about 0.9920 parts and 0.9980 parts of a silicone containing material; and
      (3) within the range of between about 0.2 parts and 0.8 parts ammonium heparin.

7. The method of claim 6, further characterized by
   (a) said ammonium heparin is present within the range of between about 0.5 parts and 0.55 parts;
   (b) said silicone containing material is present within the range of between about 0.9945 parts and 0.9950 parts; and
   (c) said deionized water is present within 98.4555 parts and 98.505 parts.

8. The method of claim 1, further characterized by
   (a) said preparing step is carried out by admixing by weight
      (1) within the range of between about 94.05 and 97.614 parts deionized water;
      (2) within the range of between about 1.4 parts and 5 parts sodium ethylene diamine tetraacetic acid; and
      (3) within the range of between about 0.950 and 0.986 parts said silicone containing material.

9. The method of claim 8, further characterized by
   (a) said sodium ethylene diamine tetraacetic acid is present within the range of between about 3.1 and 5 parts;
   (b) said silicone containing material is present within the range of between about 0.950 and 0.969 parts; and
   (c) said deionized water is present within the range of between about 94.05 and 95.931 parts.

* * * * *